(12) United States Patent
Luo et al.

(10) Patent No.: US 11,307,297 B2
(45) Date of Patent: Apr. 19, 2022

(54) METHOD AND DEVICE FOR ULTRASONIC IMAGING BY SYNTHETIC FOCUSING

(71) Applicant: TSINGHUA UNIVERSITY, Beijing (CN)

(72) Inventors: Jianwen Luo, Beijing (CN); Jing Liu, Beijing (CN); Qiong He, Beijing (CN)

(73) Assignee: TSINGHUA UNIVERSITY, Beijing (CN)

( * ) Notice: Subject to any disclaimer, the term of this patent is extended or adjusted under 35 U.S.C. 154(b) by 1106 days.

(21) Appl. No.: 15/526,305

(22) PCT Filed: Sep. 6, 2015

(86) PCT No.: PCT/CN2015/089005
§ 371 (c)(1),
(2) Date: May 11, 2017

(87) PCT Pub. No.: WO2016/155239
PCT Pub. Date: Oct. 6, 2016

(65) Prior Publication Data
US 2017/0336500 A1    Nov. 23, 2017

(30) Foreign Application Priority Data
Mar. 27, 2015    (CN) .......................... 201510142749.4

(51) Int. Cl.
*G03B 42/06*    (2021.01)
*G01S 7/52*    (2006.01)
(Continued)

(52) U.S. Cl.
CPC .......... *G01S 7/52023* (2013.01); *A61B 8/145* (2013.01); *A61B 8/5207* (2013.01);
(Continued)

(58) Field of Classification Search
None
See application file for complete search history.

(56) References Cited

U.S. PATENT DOCUMENTS 6,135,961 A * 10/2000 Pflugrath ................. A61B 8/00
600/447
7,133,699 B1 * 11/2006 Owechko .................. G01S 3/74
455/562.1
(Continued)

FOREIGN PATENT DOCUMENTS

CN        1650190 A    8/2005
CN        102028499 A    4/2011
(Continued)

OTHER PUBLICATIONS

Reeves, Stanley J. "An efficient implementation of the backward greedy algorithm for sparse signal reconstruction." IEEE Signal Processing Letters 6.10 (1999): 266-268. (Year: 1999).*
(Continued)

*Primary Examiner* — Isam A Alsomiri
*Assistant Examiner* — Jonathan D Armstrong
(74) *Attorney, Agent, or Firm* — Zilka-Kotab, P.C.

(57) ABSTRACT

Provided are a method and device for ultrasonic imaging by synthetic focusing. The method comprises: exciting a plurality of matrix elements of an ultrasonic probe to transmit plane waves many times, wherein transmitting apodizations at the time of every transmission of the plane waves by the plurality of matrix elements correspond to the respective lines in a measurement matrix in which elements are randomly distributed; after every transmission of the plane waves, exciting all the matrix elements of the ultrasonic probe to receive echo signals, in order to obtain channel data; recovering a synthetic focusing channel data set by use of a compressed sensing reconstruction algorithm according to a channel data set and the measurement matrix; and
(Continued)

subjecting the synthetic focusing channel data set to beamforming so as to generate an ultrasonic image.

14 Claims, 4 Drawing Sheets

(51) Int. Cl.
  *G01S 15/89* (2006.01)
  *A61B 8/14* (2006.01)
  *A61B 8/08* (2006.01)
  *G06T 11/00* (2006.01)

(52) U.S. Cl.
  CPC ...... *G01S 7/52025* (2013.01); *G01S 7/52085* (2013.01); *G01S 15/8997* (2013.01); *G06T 11/003* (2013.01)

(56) References Cited

U.S. PATENT DOCUMENTS

| | | | | |
|---|---|---|---|---|
| 8,824,544 | B2* | 9/2014 | Nguyen | G01S 13/0209 375/224 |
| 8,861,588 | B2* | 10/2014 | Nguyen | G01S 13/90 341/155 |
| 9,172,476 | B2* | 10/2015 | Nguyen | G01S 13/0209 |
| 9,638,798 | B2* | 5/2017 | Jensen | B06B 1/0629 |
| 9,857,463 | B2* | 1/2018 | Nogueira-Nine | G01S 13/26 |
| 10,226,234 | B2* | 3/2019 | Specht | G01S 15/8913 |
| 2002/0022780 | A1* | 2/2002 | Kawagishi | G01S 7/52049 600/443 |
| 2003/0142587 | A1* | 7/2003 | Zeitzew | G01S 7/52004 367/127 |
| 2005/0213777 | A1* | 9/2005 | Zador | H04R 25/40 381/94.1 |
| 2006/0132345 | A1* | 6/2006 | Raz | H03M 1/1235 341/155 |
| 2007/0202919 | A1* | 8/2007 | Shu | G01S 3/74 455/562.1 |
| 2007/0293752 | A1 | 12/2007 | Simpkin | |
| 2008/0129560 | A1* | 6/2008 | Baraniuk | G06K 9/0057 341/87 |
| 2010/0302086 | A1* | 12/2010 | Dudgeon | G06K 9/6289 341/155 |
| 2010/0310011 | A1* | 12/2010 | Sexton | H03M 1/129 375/316 |
| 2010/0329529 | A1* | 12/2010 | Feldman | G06K 9/6252 382/131 |
| 2011/0044524 | A1* | 2/2011 | Wang | G01R 33/54 382/131 |
| 2011/0112784 | A1* | 5/2011 | Nikitin | H03H 11/0405 702/70 |
| 2013/0236115 | A1* | 9/2013 | Nguyen | G01S 13/0209 382/260 |
| 2014/0180099 | A1* | 6/2014 | Rothberg | A61B 8/4477 600/439 |
| 2014/0247181 | A1* | 9/2014 | Nogueira-Nine | G01S 13/26 342/128 |
| 2015/0359512 | A1* | 12/2015 | Boctor | G01S 15/8997 600/444 |
| 2016/0242690 | A1* | 8/2016 | Principe | A61B 5/04012 |
| 2017/0336500 | A1* | 11/2017 | Luo | A61B 8/145 |
| 2019/0129026 | A1* | 5/2019 | Sumi | G01S 13/90 |

FOREIGN PATENT DOCUMENTS

| | | |
|---|---|---|
| CN | 102279394 A | 12/2011 |
| CN | 102288968 A | 12/2011 |
| CN | 102435992 A | 5/2012 |
| CN | 102920478 A | 2/2013 |
| CN | 103679762 A | 3/2014 |
| CN | 104306022 A | 1/2015 |
| CN | 104306023 A | 1/2015 |
| CN | 104318619 A | 1/2015 |
| CN | 104688271 A | 6/2015 |

OTHER PUBLICATIONS

Daubechies, Ingrid, et al. "Iteratively reweighted least squares minimization for sparse recovery." Communications on Pure and Applied Mathematics: A Journal Issued by the Courant Institute of Mathematical Sciences 63.1 (2010): 1-38. (Year: 2010).*
Huang, Honglin, and Anamitra Makur. "Backtracking-based matching pursuit method for sparse signal reconstruction." IEEE Signal Processing Letters 18.7 (2011): 391-394. (Year: 2011).*
Lv, Yi, and Wentao Wu. "Compressive Ultrasound Imaging Based on Analog to Information Conversion." 2012 International Conference on Biomedical Engineering and Biotechnology. IEEE, 2012. (Year: 2012).*
Chernyakova et al., "Fourier-Domain Beamforming: The Path to Compressed Ultrasound Imaging," IEEE Transactions on Ultrasonics, Ferroelectrics, and Frequency Control, vol. 61, No. 08, Aug. 2014, pp. 1252-1267.
Tur et al., "Innovation Rate Sampling of Pulse Streams With Application to Ultrasound Imaging," IEEE Transactions on Signal Processing, vol. 59, No. 04, Apr. 2011, pp. 1827-1842.
Yan-Zhen et al., "A Portable B-mode Ultrasound Imaging Method Using Synthetic Focusing," Computer Engineering, vol. 40, No. 1, Jan. 2014, pp. 246-249.
Longlong et al., "Self-adaptive Beamforming Method Based on Plane Wave Ultrasound Imaging," Journal of Biomedical Engineering, vol. 30, Aug. 2013, pp. 1-10.
Yi et al., "The application of compressed sensing in synthetic transmit aperture medical ultrasound imaging," Acta Acustica, vol. 38, No. 4, 2013, pp. 1-11.
Liebgott et al., "Pre-beamformed RF signal reconstruction in medical ultrasound using compressive sensing," Ultrasonics, vol. 53, 2013, pp. 525-533.
Du et al., "A Portable B-mode Ultrasound Imaging Method Using Synthetic Focusing," Computer Engineering, vol. 40, No. 1, Jan. 2014, pp. 246-249.
Office Action from Chinese Patent Application No. 201510142749.4, dated Aug. 1, 2016.
International Search Report from PCT Application No. PCT/CN2015/089005, dated Dec. 23, 2015.
Examination Report from European Application No. 15887196.2, dated Dec. 15, 2017.
Supplemental Examination Report from European Application No. 15887196.2, dated Oct. 17, 2020.
Schiffner et al., "Compensating the Combined Effects of Absorption and Dispersion in Plane Wave Pulse-Echo Ultrasound Imaging Using Sparse Recovery," Proceedings of the IEEE International Ultrasonics Symposium, 2013, 6 pages.
Liu et al., "A Compressed Sensing Strategy for Synthetic Transmit Aperture Ultrasound Imaging," IEEE Transactions on Medical Imaging, vol. 36, No. 4, 2017, 1 page, abstract only.

* cited by examiner

METHOD AND DEVICE FOR ULTRASONIC IMAGING BY SYNTHETIC FOCUSING

RELATED APPLICATIONS

The present application is a national phase entry of, and claims priority to, PCT Patent Application No. PCT/CN2015/089005, filed Sep. 6, 2015, which in turn claims the benefit of priority from Chinese Patent Application No. 2015/10142749.4, filed Mar. 27, 2015. The subject matter of each of the foregoing priority applications is hereby incorporated by reference in its entirety.

FIELD OF INVENTION

The present invention relates to the field of ultrasound imaging, and more particularly to a synthetic focusing ultrasound imaging method and apparatus.

BACKGROUND

The ultrasound imaging is widely used for clinical diagnosis because it has the advantages of being real time, inexpensive, noninvasive, non-ionizing, etc. Spatial resolution, temporal resolution and contrast are three criteria used to evaluate ultrasound images, and ultrasound images with high spatiotemporal resolution and high contrast can better assist in clinical diagnosis. But unfortunately, these three criteria cannot reach their best at the same time.

In the process of traditional ultrasound imaging, an image scanning line is obtained by transmitting focused beam. Images obtained in this mode have relatively high spatial resolution and contrast resolution, especially near transmit focal zones. However, the frame rate, i.e., temporal resolution, in this mode is not high enough because an image usually requires hundreds of scanning lines and thereby requires hundreds of transmissions. Although reduction of the number of focal zones for each transmission can increase the frame rate effectively, this causes deterioration of the spatial resolution and the contrast.

Synthetic focusing method, as a synthetic aperture method, was proposed to improve spatial resolution of ultrasound images in 1992. In the synthetic focusing method, for an ultrasound probe with 128 elements, each element is sequentially activated to transmit ultrasound waves, and all elements receive echo signals after each element transmitting ultrasound waves. FIG. 1 illustrates a schematic diagram of the prior synthetic focusing ultrasound imaging and extraction of an original signal x therein. The oblique straight lines denote ultrasound probes. The black rectangular blocks on the oblique straight lines denote activated elements on each transmission in synthetic focusing mode, while other elements on the probe are not activated. The upward solid arrows denote a process of receiving echo signals. FIG. 1 shows that transmission and reception event are executed n times, and the rightward dotted arrow denotes a process of extracting the original signal x. For an ultrasound probe with 128 elements, n is 128. A low-quality ultrasound image is formed in each transmission and reception. A high-quality image can be obtained according to n low-quality images. In particular, synthetic focusing channel data received by all elements in the $i^{th}$ time is represented by a matrix $X_i$. There are $2*d*fs/c$ rows and 128 columns in the matrix $X_i$, wherein d is the sampling depth, fs is the sampling frequency, c is the speed of sound. Each column in the matrix $X_i$ corresponds to echo signals received by its corresponding elements. After n times of transmission and reception, dataset $X:\{X_1, X_2, \ldots X_n\}$ is a synthetic focusing channel dataset, which is a set of synthetic focusing channel data $X_i$.

Because the synthetic focusing method can achieve full dynamic focusing in both directions of transmission and reception, so the ultrasound images obtained by this method have very high spatial resolution. Its resolution is equivalent to that obtained by using an infinite number of transmit focal zones in the traditional mode. However, in the synthetic focusing method, only one element is activated each event, and the energy is very low, therefore the contrast of the obtained ultrasound images is not high. Based on this, a synthetic transmit aperture method is proposed to improve the contrast of ultrasound images. In ultrasound imaging based on the synthetic transmit aperture method, an array is divided into a plurality of sub-apertures, each of which is constituted by a plurality of continuous elements. An ultrasound image is obtained by sequentially activating each sub-aperture to transmit ultrasound waves and receiving echo signals by all elements. Compared with the synthetic focusing method, this method improves the image contrast because more elements are activated in each event, and it can obtain the higher frame rate because of fewer times of transmission. But this method sacrifices the spatial resolution.

SUMMARY OF THE INVENTION

In order to solve the above technical problems at least in part, in one aspect of the present invention, a synthetic focusing ultrasound imaging method is provided. The method includes: activating a plurality of elements of an ultrasound probe to transmit plane waves multiple times, wherein transmit apodizations formed in each event that the plurality of elements transmit plane waves correspond to a corresponding row in a measurement matrix where elements obey a random distribution; after each plane wave transmission, activating all elements of the ultrasound probe to receive echo signals to obtain channel data; recovering a synthetic focusing channel dataset by utilizing a compressed sensing reconstruction algorithm according to the channel dataset and the measurement matrix; and beamforming the synthetic focusing channel dataset to generate an ultrasound image.

Optionally, the random distribution is a random distribution ranging from 0 to 1.

Optionally, the recovering a synthetic focusing channel dataset further includes: calculating a sparse representation of a signal to be recovered by utilizing the compressed sensing reconstruction algorithm according to the channel dataset, the measurement matrix and a sparse basis; and performing an inverse parse transform on the sparse representation of the signal to be recovered by utilizing the sparse basis to recover the synthetic focusing channel dataset.

Optionally, the sparse basis is a wavelet basis.

Optionally, the calculating a sparse representation of a signal to be recovered is performed by utilizing a $l_1$ norm minimum solution method.

Optionally, a measurement signal extracted from the channel dataset in a slow time domain is normalized before the calculating a sparse representation of a signal to be recovered; and values are recovered from a result of the inverse sparse transform after the inverse sparse transform.

Optionally, in the case that an element in a $m^{th}$ row and a $n^{th}$ column in each matrix in the channel dataset is 0, an element in a $m^{th}$ row and a $n^{th}$ column in each matrix in the synthetic focusing channel dataset is set to 0 directly.

In another aspect of the present invention, a synthetic focusing ultrasound imaging apparatus is also provided. The apparatus includes: an activation transmission module for activating a plurality of elements of an ultrasound probe to transmit plane waves multiple times, wherein transmit apodizations formed in each event that the plurality of elements transmit plane waves correspond to a corresponding row in a measurement matrix where elements obey a random distribution; an activation acquisition module for activating all elements of the ultrasound probe to receive echo signals to obtain channel data after each plane wave transmission; a data recovery module for recovering a synthetic focusing channel dataset by utilizing a compressed sensing reconstruction algorithm according to the channel dataset and the measurement matrix; and an image reconstruction module for beamforming the synthetic focusing channel dataset to generate an ultrasound image.

Optionally, the random distribution is a random distribution ranging from 0 to 1.

Optionally, the data recovery module further includes: a first calculation module for calculating a sparse representation of a signal to be recovered by utilizing the compressed sensing reconstruction algorithm according to the channel dataset, the measurement matrix and a sparse basis; and a second calculation module for performing an inverse parse transform on the sparse representation of the signal to be recovered by utilizing the sparse basis to recover the synthetic focusing channel dataset.

Ultrasound images obtained by the above method and apparatus not only have very high resolution, but also have the advantages of high frame rate and high contrast because the ultrasound waves are transmitted fewer times and each transmission has high energy.

A series of simplified concepts are introduced in the contents of the present invention, they will be further explained in detail in the detailed description part. The summary of the present invention is intended to neither define key features and necessary technical features of the technical solutions claimed for protection nor determine the protection scope of the technical solutions claimed for protection.

Advantages and features of the present invention will be described in detail below in connection with the accompanying drawings.

BRIEF DESCRIPTION OF THE DRAWINGS

The following accompanying drawings, which constitute a part of the present invention hereby, help to understand the present invention. The accompanying drawings illustrate the implementations of the present invention and, together with the descriptions serve to explain the principle of the present invention.

DETAILED DESCRIPTION

In the following description, numerous details are presented so as to provide more thorough understanding of the present invention. However, those skilled in the art can appreciate that the following description only relates to preferable embodiments of the present invention, and the present invention may be implemented without one or more of these details. Additionally, some technical features well known in the art are not described so as to avoid confusion with the present invention.

The compressed sensing theory states that if a signal $x \in R^n$ is sparse or compressible in a certain domain, it can be recovered from a signal with a much lower sampling frequency than the Nyquist sampling frequency with high probability. Because of this nature, compressed sensing may be used for data compression, channel coding, inverse problem solving and data acquisition. In the field of ultrasound, application of the compressed sensing theory focuses mainly on the problem of reducing the data amount. Liebgott and Eldar's group have done a lot of research on this matter, the amount of channel data can be greatly reduced by applying compressive sampling in a fast time domain. The fast time domain is in a direction along which ultrasound echo signals are acquired. Reduction of the data amount is very helpful to portable ultrasound systems, but cannot improve frame rate. The frame rate is calculated as c/2dn, wherein c is the speed of sound, d is the imaging depth, n is the times of transmission. Once an imaging object and an imaging depth are determined, compressive sampling performed in the fast time domain cannot change the times of transmission n, that is, the frame rate is not changed. Thus, if the frame rate is expected to be improved, it can be realized by reducing the times of transmission, i.e., performing compressive sampling in the slow time domain. The slow time domain is along a transmission-reception repeating direction.

Figure 1:
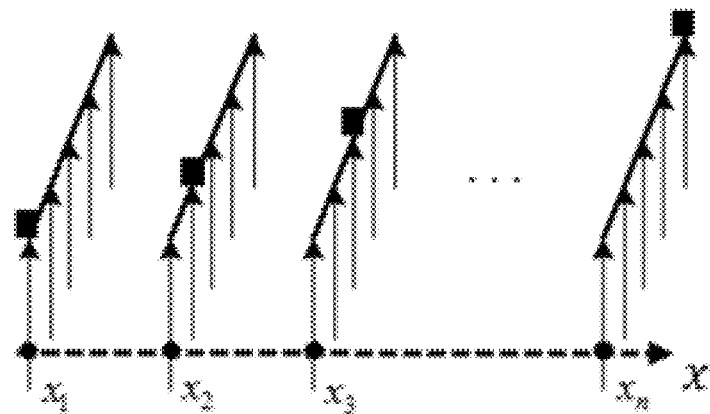
FIG. 1 illustrates a schematic diagram of the prior synthetic focusing ultrasound imaging and extraction of an original signal therein.
Figure 2:
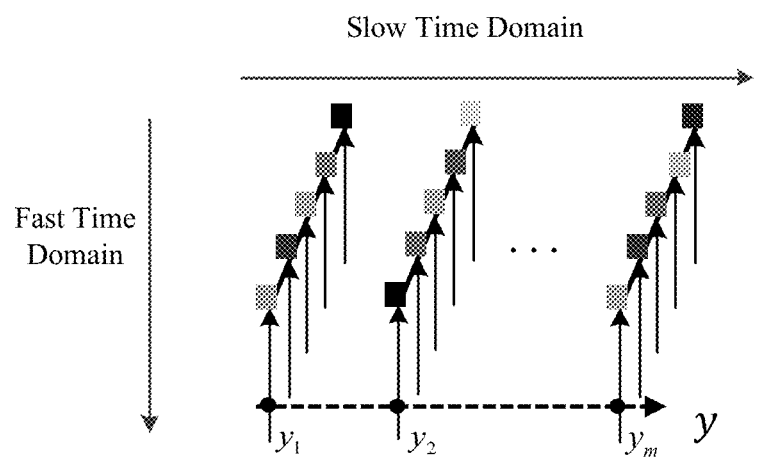
FIG. 2 illustrates a schematic diagram of synthetic focusing ultrasound imaging and extraction of a measurement signal therein according to a specific embodiment of the present invention.
Figure 3:
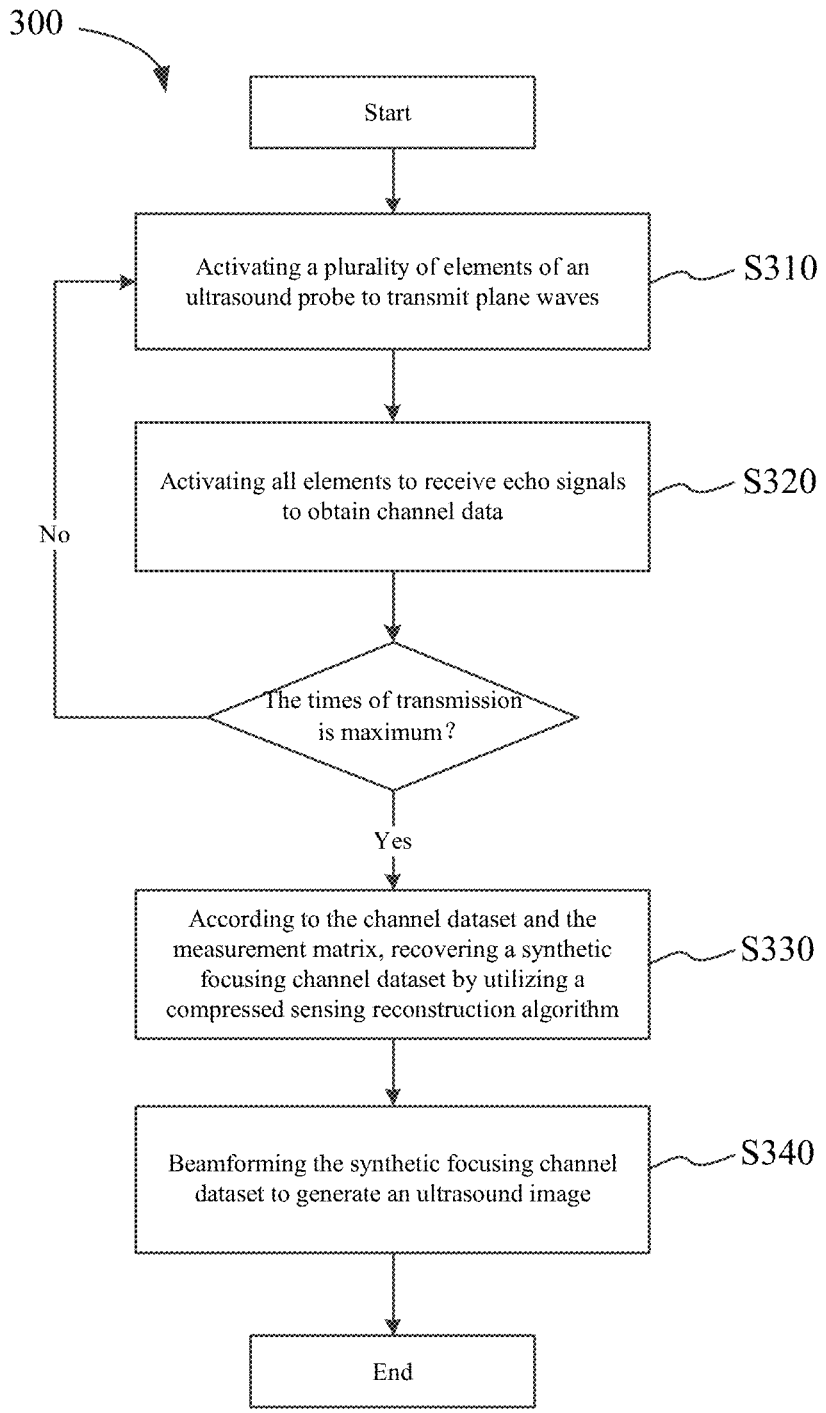
FIG. 3 is a flow chart of a synthetic focusing ultrasound imaging method according to a specific embodiment of the present invention.

The present invention applies this new theory—compressed sensing to the field of ultrasound imaging, in order to obtain ultrasound images with high frame rate, high resolution and high contrast. FIG. 2 illustrates a schematic diagram of synthetic focusing ultrasound imaging and extraction of a measurement signal y therein according to a specific embodiment of the present invention. The synthetic focusing imaging method provided by the present invention applies compressive sampling to the slow time domain shown in FIG. 2. FIG. 3 is a flow chart of a synthetic focusing ultrasound imaging method 300 according to a specific embodiment of the present invention.

As shown in FIG. 3, the synthetic focusing ultrasound imaging method 300 includes the following steps.

At S310, a plurality of elements of an ultrasound probe are activated to transmit plane waves. Transmit apodizations formed while the plurality of elements transmit plane waves correspond to a corresponding row in a measurement matrix $\Phi$ where elements obey a random distribution.

The number of columns in the measurement matrix Φ equals to the number of elements of the ultrasound probe. In an example of the present invention, take an ultrasound probe with 128 elements as example, it is assumed that all elements take part in plane wave transmission, then the number of columns in the measurement matrix Φ is 128. Elements in the measurement matrix Φ obey a random distribution. Preferably, the elements in the measurement matrix Φ obey a random distribution ranging from 0 to 1. By a random distribution ranging from 0 to 1, artifacts in the finally obtained ultrasound images can be significantly reduced, causing the images more accurate. More preferably, the elements in the measurement matrix Φ obey a uniform random distribution ranging from 0 to 1. A uniform random distribution ranging from 0 to 1 can ensure the energy of ultrasound waves during imaging is higher, and the contrast of the finally obtained ultrasound images is high, so as to facilitate users, such as doctors, etc., to observe. Optionally, the measurement matrix Φ may be a random Gauss matrix.

As shown in FIG. 2, the rectangle blocks denote the elements, and different gray levels of the rectangle blocks denote the amplitude of transmit apodizations. In the synthetic focusing mode as described above, 128 times of transmission, for example, needs to be performed and only one element is fully activated in each transmission. According to the linear acoustic filed theory, channel data obtained by transmitting plane wave once is a linear combination of channel datasets obtained by transmitting ultrasound waves by each of 128 single elements once, wherein linear coefficients are transmit apodizations formed while the probe transmits plane waves. Transmit apodizations formed in each event that plane waves are transmitted correspond to a corresponding row in the measurement matrix Φ. That is, the first row in the measurement matrix Φ is transmit apodizations formed while plane waves are transmitted for the first time, the second row is transmit apodizations formed while plane waves are transmitted for the second time, and so forth. Thus, according to the embodiment of the present invention, information obtained from 128 transmissions by activating all 128 elements sequentially may be obtained by transmitting plane waves with transmit apodizations once, that is, compressive sampling is completed in a slow time domain.

At S320, after each plane wave transmission, all elements of the ultrasound probe are activated to receive echo signals to obtain channel data $Y_i$.

The above steps S310 and S320 are repeated until the total times of transmission, e.g., 64, are accomplished. From above, a set of channel data: channel dataset Y:$\{Y_1, Y_2, \ldots Y_{64}\}$, i.e., a synthetic focusing channel dataset obtained by combining synthetic focusing method with compressed sensing reconstruction algorithm, is obtained. $Y_i$ is a matrix. The channel data $Y_i$ has the same dimension with the synthetic focusing channel data $X_i$ and the number of rows thereof equals to 2*d*fs/c. d is the sampling depth, fs is the sampling frequency, c is the speed of sound. The number of columns equals to the number of elements of the probe, and it is 128 in this embodiment. Each column represents echo signals received by each element after plane waves are transmitted.

According to the description of the step S310, one of ordinary skill in the art can understand that the number of rows in the measurement matrix Φ equals to the total times of transmission.

One of ordinary skill in the art can understand that the total times of transmission may be arbitrary number smaller than the number of elements. Preferably, the total times of transmission ranges from 32 to 112. When the imaging object is a simple dot object or the reconstruction algorithm is the Basis Pursuit (BP) algorithm, the total times of transmission ranges from 32 to 64 preferably. When the imaging object is a complex biological tissue or the reconstruction algorithm is the Orthogonal Matching Pursuit (OMP) algorithm, the total times of transmission ranges from 64 to 112 preferably.

One of ordinary skill in the art can understand that if at the step S310, not all elements take part in plane wave transmission, then the rest elements that do not take part in plane wave transmission may still respectively transmit ultrasound waves sequentially, and all elements of the ultrasound probe receive echo signals after any one thereof transmits ultrasound waves, to obtain corresponding channel data for imaging calculation, as with the prior synthetic focusing ultrasound imaging method.

At S330, a synthetic focusing channel dataset is recovered by utilizing a compressed sensing reconstruction algorithm, according to the channel dataset and the measurement matrix.

The synthetic focusing channel dataset X:$\{X_1, X_2, \ldots X_{128}\}$ is a channel dataset obtained by 128 times of transmission and reception of ultrasound waves in the prior synthetic focusing ultrasound imaging method. By utilizing the measurement matrix Φ, the synthetic focusing channel dataset can be recovered from the channel dataset Y:$\{Y_1, Y_2, \ldots Y_m\}$ in this embodiment by applying the compressed sensing reconstruction algorithm. In particular, a measurement signal y is extracted from the channel dataset Y in the slow time domain with all receive channels and all sampling depths being traversed over. A signal x to be recovered can be recovered by utilizing the compressed sensing reconstruction algorithm, according to the measurement signal y and the measurement matrix Φ. A complete synthetic focusing channel dataset can be obtained by this recovery process with all receive channels and all sampling depths being traversed over.

Employing the mathematical symbols as mentioned above, the step S330 is a process of recovering a synthetic focusing channel dataset X:$\{X_1, X_2, \ldots X_n\}$ from the channel dataset Y:$\{Y_1, Y_2, \ldots Y_m\}$, wherein n equals to the number of elements of the probe, e.g., 128.

Figure 4:
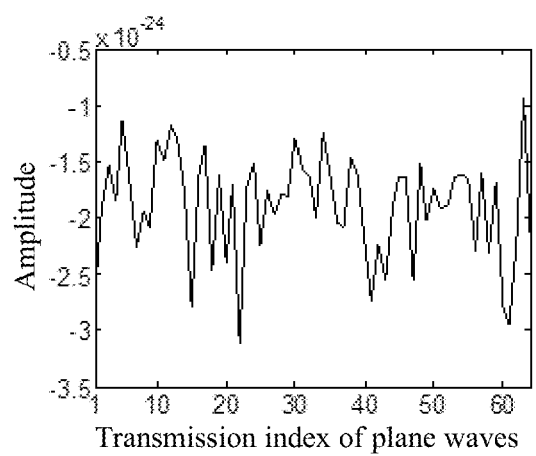
FIG. 4 illustrates a schematic diagram of a measurement signal according to a specific embodiment of the present invention.
Figure 5:
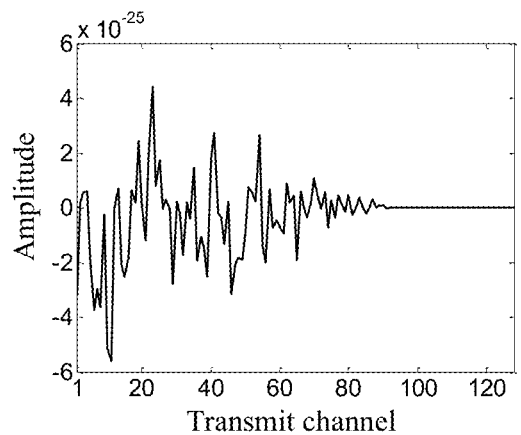
FIG. 5 illustrates a schematic diagram of a recovered signal according to a specific embodiment of the present invention.

For a first row and a first column in each matrix of $Y_1, Y_2, \ldots Y_{64}$, a measurement signal is extracted in the slow time domain, to obtain a measurement signal y=$y_1, y_2, \ldots y_{64}$ for the first row and the first column (i.e., a measurement signal for a first sampling depth and a first receive channel), wherein the exaction of $y_1, y_2, \ldots y_{64}$ is shown in FIG. 2. A signal to be recovered x=$[x_1, x_2, \ldots, x_{128}$ corresponding to the measurement signal y=$y_1, y_2, \ldots y_{64}]$ is recovered from the measurement signal y=$y_1, y_2, \ldots y_{64}$ by utilizing the compressed sensing reconstruction algorithm, and $x_i$ is written in a first row and a first column in each matrix $X_i$ in X; the above process is repeated for all rows and all columns, then the synthetic focusing channel dataset X is recovered. As such, the recovery of a synthetic focusing channel dataset X:$\{X_1, X_2, \ldots X_{128}\}$, which is obtained by 128 times of traditional synthetic focusing transmission, from a channel dataset Y:$\{y_1, y_2, \ldots y_{64}\}$ obtained by 64 times of plane wave transmission is realized. FIG. 4 and FIG. 5 illustrate schematic diagrams of a measurement signal and a recovered signal according to a specific embodiment of the present invention respectively. The vertical ordinates in FIG. 4 and FIG. 5 are both the amplitude of signals. The horizontal ordinate in FIG. 4 is transmission index of plane waves. The horizontal ordinate in FIG. 5 represents the synthetic focusing transmit channel.

Figure 6:
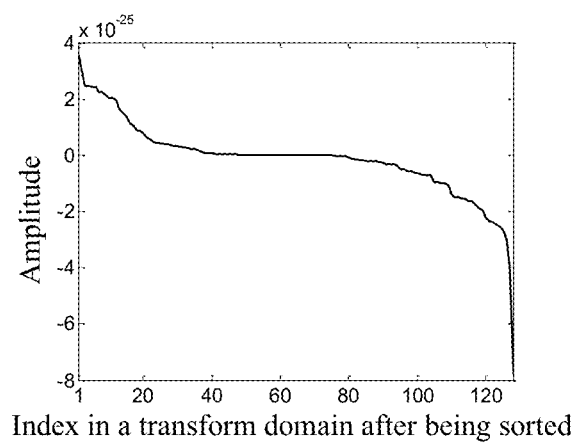
FIG. 6 illustrates a schematic diagram of a sparse representation of a signal to be recovered according to a specific embodiment of the present invention.

The compressed sensing theory states that if a signal x is sparse or compressible in a certain domain, that is X=Ψv (Formula 1), wherein $\Psi \in C^{128 \times 128}$ a sparse basis, and only a few elements of v are non-zero or a seriation of elements of v obeys an exponential decay, then the signal x can be recovered from a few of its linear measurement signals y=Φx (Formula 2), wherein Φ is a measurement matrix. In this embodiment, according to the linear acoustic field theory, each row in the measurement matrix Φ corresponds to transmit apodizations. The above sparse basis Ψ may be a wavelet basis. For example, the sparse basis Ψ may be a sym8 wavelet basis. The wavelet basis can better sparsely represent ultrasound signals extracted in the slow time domain, the signal recovery effect is better and the imaging frame rate is higher. FIG. 6 illustrates a schematic diagram of a sparse representation v of a signal to be recovered according to a specific embodiment of the present invention, wherein the vertical ordinate represents the amplitude of the signal, and the horizontal ordinate represents the index in a transform domain after being sorted.

At S340, the synthetic focusing channel dataset is beamformed to generate an ultrasound image.

The step S340 can employ the existing beamforming method, and one ordinary of skill in the art can understand the implementation of this step, so for the sake of brevity, no more details will be explained here.

In an embodiment of the present invention, by utilizing the principle of one plane wave transmission being a compressive sampling of complete synthetic focusing, ultrasound waves may be transmitted fewer times, the compressive sampling is successfully realized in the slow time domain, and the frame rate of images is improved, compared with the prior synthetic focusing ultrasound imaging method. At the same time, because all elements are activated in one plane wave transmission, the energy is higher, so the contrast of images is also improved. Because what is obtained by the above method is a synthetic focusing image, so the image's characteristic of high resolution is retained. In a word, ultrasound images with high frame rate, high resolution and high contrast are obtained by utilizing the compressed sensing technology.

Additionally, the above method has universality in the field of ultrasound imaging, especially in some applications which require higher imaging frame rate and higher imaging quality, such as the real-time three-dimensional ultrasound imaging, the cardiovascular imaging, etc. Besides the traditional structure imaging, this method can be also helpful for providing the high-quality ultrasound functional imaging, such as the cardiovascular elasticity imaging, etc.

According to a specific embodiment of the present invention, the operation of recovering the synthetic focusing channel dataset in the above step S330 may further include the following sub-steps.

At S331, a sparse representation v of a signal x to be recovered is calculated according to the channel dataset Y, the measurement matrix Φ and the sparse basis Ψ.

A measurement signal y is extracted from the channel dataset Y in the slow time domain. The above Formula 1 is substituted into the Formula 2, to obtain the measurement signal y=ΦΨv=Θv (Formula 3). The sparse representation v of the signal x to be recovered can be calculated according to the Formula 3.

A $l_1$ norm minimum solution method may be used to calculate v.

$$V = \underset{V \in R^n}{\mathrm{argmin}} \|V\|_1,$$

wherein $\|y-\Theta v\|_2 \leq \varepsilon$

ε is a tolerated error. There are many solution methods for $l_1$ norm minimization. Preferably, a Basis Pursuit algorithm is employed to perform the solution. This method may make the calculated result of the measurement signal y more accurate, thereby obtaining a more accurate reconstructed image. Optionally, an Orthogonal Matching Pursuit is employed to perform the solution. Optimization of $l_1$ norm minimization is a good approximation of $l_0$ norm minimization problem (the sparse problem), and a difficult $l_0$ norm minimization problem can be solved by utilizing the $l_1$ norm minimization optimization method with a high probability. Thus, the resolution of the generated ultrasound image may be ensured higher.

At S332, an inverse sparse transform is performed on the sparse representation v of the signal x to be recovered by utilizing the sparse basis Ψ, to recover a synthetic focusing channel dataset X.

According to the sparse representation v of the signal x to be recovered and the sparse basis Ψ, the recovered signal x can be obtained by substituting the sparse representation v and the sparse basis Ψ into the Formula (1) x=Ψv. All the recovered signals x compose the synthetic focusing channel dataset X.

Optionally, the measurement signal y extracted from the channel dataset Y in the slow time domain is normalized before calculating the sparse representation of the signal to be recovered, and values are recovered from a result of the inverse sparse transform after the inverse sparse transform. Optionally, the measurement signal y is normalized firstly, and a maximum value $y_{max}$ is saved. It is assumed that the sparse basis is an sym8 wavelet basis, and ε is 1e-3, the result obtained by the inverse sparse transform is multiplied by the real part of $y_{max}$ to obtain the recovered signal x. By doing so, an exact solution can be guaranteed even if the signal intensity is very low. In the case that the signal intensity is very high, the tolerated error ε is able to be rationalized. The normalization operation better ensures an accurate reconstruction of signals and makes the imaging effect more stable.

Optionally, in the case that an element in a $m^{th}$ row and a $n^{th}$ column in each matrix in the channel dataset Y is 0, an element in a $m^{th}$ row and a $n^{th}$ column in each matrix in the synthetic focusing channel dataset X is set to 0 directly. This can simplify calculation and improve efficiency.

Figure 7:
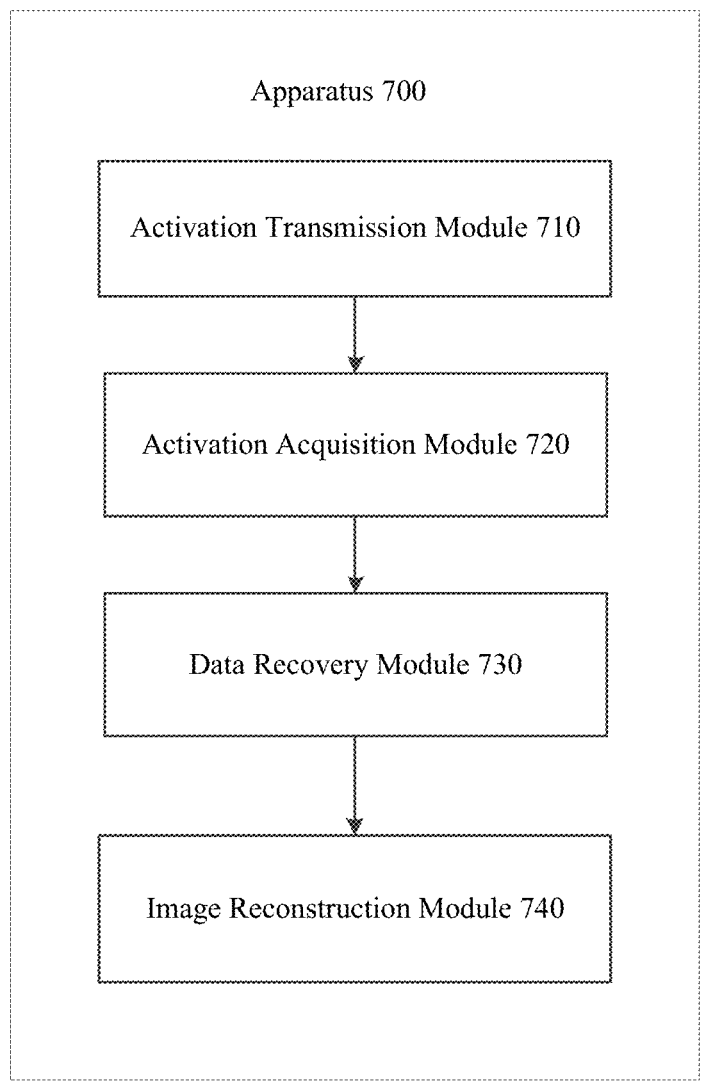
FIG. 7 illustrates a schematic block diagram of a synthetic focusing ultrasound imaging apparatus according to a specific embodiment of the present invention.

According to another aspect of the present invention, a synthetic focusing ultrasound imaging apparatus is also provided. FIG. 7 illustrates a block diagram of a synthetic focusing ultrasound imaging apparatus 700 according to a specific embodiment of the present invention. As shown in FIG. 7, the apparatus 700 includes an activation transmission module 710, an activation acquisition module 720, a data recovery module 730 and an image reconstruction module 740.

The activation transmission module 710 is used to activate a plurality of elements of an ultrasound probe to transmit plane waves multiple times, wherein transmit apodizations formed in each event that the plurality of elements transmit plane waves correspond to a corresponding row in a measurement matrix where elements obey a random distribution. The activation acquisition module 720 is used to activate all elements of the ultrasound probe to receive echo signals to obtain channel data after each plane wave transmission. The data recovery module 730 is used to recover a synthetic focusing channel dataset by utilizing a compressed sensing reconstruction algorithm according to the channel dataset and the measurement matrix. The image reconstruction module 740 is used to beamform the synthetic focusing channel dataset to generate an ultrasound image.

Optionally, the above random distribution is a random distribution ranging from 0 to 1.

Optionally, the above data recovery module 730 further includes a first calculation module and a second calculation module. The first calculation module is used to calculate a sparse representation of a signal to be recovered by utilizing the compressed sensing reconstruction algorithm according to the channel dataset, the measurement matrix and a sparse basis. The second calculation module is used to perform an inverse parse transform on the sparse representation of the signal to be recovered by utilizing the sparse basis to recover the synthetic focusing channel dataset.

By reading the above description regarding the synthetic focusing ultrasound imaging method, one ordinary of skill in the art can understand the composition, implementation, and technical effect of the synthetic focusing ultrasound imaging apparatus, thus no more details will be explained here for the sake of brevity.

The present invention has been explained by the above embodiments, but it should be appreciated that the above embodiments are just used for examples and illustration purposes, rather than to be intended to limit the invention to the scope of the described embodiments. Additionally, those skilled in the art can understand that the present invention is not limited to the above embodiments and many modifications and variations are possible in view of the teachings of the present invention and all fall into the protection scope of the present invention. The protection scope of the present invention should be construed according to the accompanying claims and their equivalents.

What is claimed is:

1. A synthetic focusing ultrasound imaging method, including:
    activating a plurality of elements of an ultrasound probe to transmit plane waves multiple times, wherein transmit apodizations are formed in each event that the plurality of transmit plane waves correspond to a row in a measurement matrix, wherein elements of the measurement matrix obey a random distribution;
    after each plane wave transmission, activating all elements of the ultrasound probe to receive echo signals to obtain channel data;
    recovering a synthetic focusing channel dataset by utilizing a compressed sensing reconstruction algorithm according to a channel dataset and the measurement matrix, wherein the channel dataset is a set of the channel data; and
    beamforming the synthetic focusing channel dataset to generate an ultrasound image.

2. The method according to claim 1, wherein the random distribution is a random distribution ranging from 0 to 1.

3. The method according to claim 1, wherein recovering the synthetic focusing channel dataset further includes:
    calculating a sparse representation of a signal to be recovered by utilizing the compressed sensing reconstruction algorithm according to: the channel dataset, the measurement matrix and a sparse basis; and
    performing an inverse sparse transform on the sparse representation of the signal to be recovered by utilizing the sparse basis to recover the synthetic focusing channel dataset.

4. The method according to claim 3, wherein the sparse basis is a wavelet basis.

5. The method according to claim 3, wherein calculating $l_1$ norm minimum solution method.

6. The method according to claim 3, wherein a measurement signal extracted from the channel dataset in a slow time domain is normalized before calculating the sparse representation of a signal to be recovered; and
    wherein one or more values are recovered from a result of the inverse sparse transform after performing the inverse sparse transform.

7. The method according to claim 1, wherein in response to determining an element in a $m^{th}$ row and a $n^{th}$ column in each matrix in the channel dataset is 0, an element in a $m^{th}$ row and a $n^{th}$ column in each matrix in the synthetic focusing channel dataset is set to 0 directly.

8. A synthetic focusing ultrasound imaging apparatus, including:
    an activation transmission module for activating a plurality of elements of an ultrasound probe to transmit plane waves multiple times, wherein transmit apodizations are formed in each event that the plurality of transmit plane waves correspond to a row in a measurement matrix, wherein elements of the measurement matrix obey a random distribution;
    an activation acquisition module for activating all elements of the ultrasound probe to receive echo signals to obtain channel data after each plane wave transmission;
    a data recovery module for recovering a synthetic focusing channel dataset by utilizing a compressed sensing reconstruction algorithm according to a channel dataset and the measurement matrix, wherein the channel dataset is a set of the channel data; and
    an image reconstruction module for beamforming the synthetic focusing channel dataset to generate an ultrasound image.

9. The apparatus according to claim 8, wherein the random distribution is a random distribution ranging from 0 to 1.

10. The apparatus according to claim 8, wherein the data recovery module further includes:
    a first calculation module for calculating a sparse representation of a signal to be recovered by utilizing the compressed sensing reconstruction algorithm according to the channel dataset, the measurement matrix and a sparse basis; and
    a second calculation module for performing an inverse sparse transform, on the sparse representation of the signal to be recovered, by utilizing the sparse basis to recover the synthetic focusing channel dataset.

11. The apparatus according to claim 10, wherein the sparse basis is a wavelet basis.

12. The apparatus according to claim 10, wherein the first calculation module calculates the sparse representation of the signal to be recovered by utilizing a $l_1$ norm minimum solution method.

13. The apparatus according to claim 10, wherein a measurement signal extracted from the channel dataset in a slow time domain is normalized before the calculating a sparse representation of a signal to be recovered; and
    wherein one or more values are recovered from a result of the inverse sparse transform after performing the inverse sparse transform.

14. The apparatus according to claim 8, wherein in response to determining an element in a $m^{th}$ row and a $n^{th}$ column in each matrix in the channel dataset is 0, an element in a $m^{th}$ row and a $n^{th}$ column in each matrix in the synthetic focusing channel dataset is set to 0 directly.

\* \* \* \* \*